United States Patent
Bagala'Rampazzo et al.

(10) Patent No.: US 8,614,357 B2
(45) Date of Patent: Dec. 24, 2013

(54) OLIGOMERIC DERIVATIVES OF SPIROBIFLUORENE, THEIR PREPARATION AND USE

(75) Inventors: Liliana Bagala'Rampazzo, Rom (IT); Giulia Fioravanti, Rom (IT); Leonardo Mattiello, Rom (IT)

(73) Assignee: Merck Patent GmbH, Darmstadt (DE)

( * ) Notice: Subject to any disclaimer, the term of this patent is extended or adjusted under 35 U.S.C. 154(b) by 1427 days.

(21) Appl. No.: 11/632,337

(22) PCT Filed: Jul. 15, 2005

(86) PCT No.: PCT/EP2005/007746
§ 371 (c)(1),
(2), (4) Date: Oct. 29, 2008

(87) PCT Pub. No.: WO2006/005627
PCT Pub. Date: Jan. 19, 2006

(65) Prior Publication Data
US 2009/0234164 A1   Sep. 17, 2009

(30) Foreign Application Priority Data
Jul. 15, 2004 (IT) .............................. RM2004A0352

(51) Int. Cl.
| C07C 49/00 | (2006.01) |
| C07C 315/00 | (2006.01) |
| C07C 317/00 | (2006.01) |
| C07C 319/00 | (2006.01) |
| C07C 331/00 | (2006.01) |
| C07C 381/00 | (2006.01) |
| H01L 29/08 | (2006.01) |
| H01L 35/24 | (2006.01) |
| H01L 51/00 | (2006.01) |

(52) U.S. Cl.
USPC .............. 568/303; 568/18; 568/308; 257/40; 257/E51.049; 428/917

(58) Field of Classification Search
None
See application file for complete search history.

(56) References Cited

U.S. PATENT DOCUMENTS

| 5,840,217 A * | 11/1998 | Lupo et al. ..................... 252/583 |
| 6,822,094 B2 * | 11/2004 | Salbeck et al. ................. 544/230 |
| 7,345,301 B2 * | 3/2008 | Gerhard et al. ................. 257/40 |
| 7,557,249 B2 * | 7/2009 | Bagala' Rampazzo et al. ............. 568/326 |
| 2003/0065190 A1 | 4/2003 | Spreitzer et al. |
| 2006/0255332 A1 | 11/2006 | Becker et al. |

FOREIGN PATENT DOCUMENTS

| DE | 103 17556 | 11/2004 |
| EP | 676461 | 3/1995 |
| WO | WO-2004/013080 | 2/2004 |
| WO | WO 2004/093207 | * 10/2004 |
| WO | WO-2005/034260 | 4/2005 |

OTHER PUBLICATIONS

Haas, G., et al., "Optisch Aktive 9,9'—Spirobifluoren-Derivate", Helvetica Chimica Acta, 1969, vol. 52, No. 5, pp. 1202-1218.
Aviram, A., "Molecules for Memory, Logic, and Amplification", J. Am. Chem. Soc., 1988, vol. 110, pp. 5687-5692.
Laquindanum, J. G., et al., "n-Channel Organic Transistor Materials Based on Naphthalene Frameworks", J. Am. Chem. Soc., 1996, vol. 188, pp. 11331-11332.
Gore, P. H., "The Friedel-Crafts Acylation Reaction and its Application to Polycyclic Aromatic Hydrocarbons", The Friedel-Cafts Acylation Reaction, 1954, pp. 229-281.

* cited by examiner

Primary Examiner — Clinton Brooks
(74) Attorney, Agent, or Firm — Novak Druce Connolly Bove + Quigg LLP

(57) ABSTRACT

SBF derivatives, represented with the following formula: SBF-X wherein:

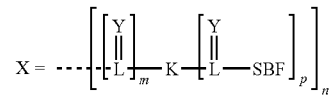

with
m=0, 1, 2 or 3;
p=positive integer,;
n=positive integer;
L: is the same or different and independently represents C, PR, AsR, SbR, BiR, S, Se, Te, S=Y, Se=Y or Te=Y;
Y: is the same or different and independently represents O, S, Se or Te; K: is the same or different and independently represents a chemical bond or a group selected from O, S, $BR_{(2-p)}$, N, $NR_{(2-p)}$, $R_{(2-p)}P=O$, $B_3O_3$, $(PR)_3N_3$, $CR_{(3-p)}$, $CR_{(3-p)}(C_6H_4)_{(p+1)}$, $SiR_{(3-p)}(C_6H_4)_{(p+1)}$ alkyne, substituted alkyne, alkyne, substituted alkyne, aromatic or R substituted aromatic, heteroaromatic-or a combination of two, three or four of the above mentioned groups; SBF: spiro-compound of formula (I):

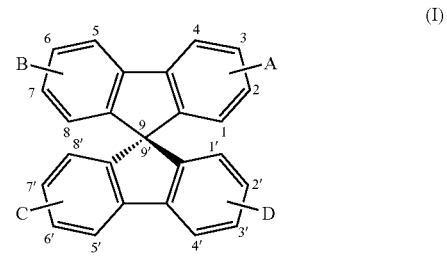

R, A, B, C, D: is the same or different and independently represents H, deuterium, F, Cl, Br, I, CN, a linear, branched or cyclic alkyl, alkoxy or thioalkoxy chain, or a combination from two, three or four of these systems; two or more substituents R can form a further monocyclic or polycyclic aliphatic or aromatic ring system with each other.

17 Claims, No Drawings

OLIGOMERIC DERIVATIVES OF SPIROBIFLUORENE, THEIR PREPARATION AND USE

RELATED APPLICATIONS

This application is a national stage application (under 35 U.S.C. 371) of PCT/EP2005/007746 filed Jul. 15, 2005, which claims the benefit of Italian application RM2004A000352 filed Jul. 15, 2004.

FIELD OF THE INVENTION

The present invention relates to oligomeric derivatives of spirobifluorene of general formula SBF-X, wherein the SBF group and the X term are specified below. The invention also relates to the synthesis method of said compounds and their use, in particular their use as materials in the field of molecular electronics.

KNOWN ART

Spirobifluorenes (SBF) are a class of spiro-compounds well known in organic chemistry, [(9,9'-spirobi[9H-fluorene])]. Their molecular structure is composed of two identical halves, each one of conjugated aromatic type, bond together by a quaternary $sp^3$ carbon atom. The consequences of these features are: the two halves of the molecule are in mutually perpendicular; said two halves cannot be considered conjugated to each other in the classical meaning of the term.

The preparation of these compounds is described by Prelog (1) and their application features are described in Aviram (2), as well as in EP 0676461.

SBFs are among those classes of organic molecules which can be used in the arrangement and realization of electronic circuits and switches for organic electronic devices.

SBF derivatives are described in WO 04/013080, however these compounds are not all satisfactory for the applications which include blue light OLEDs as well as OLEDs emitting light from the triplet excited state.

US 2003/0065190 discloses some SBF derivatives to be used, for example, as electroluminescence materials; however these compounds are not all satisfactory with respect to the solubility features in common organic solvents, the electron acceptance of one or more electrons and the molecular symmetry, properties which are considered to be advantageous for the uses described below.

The inventors have now found a class of compounds, SBF derivatives, which exhibits particularly interesting physical-chemical features with respect to the known art for the use in the field of molecular electronics, especially in OLEDs, with the general term of molecular electronics meaning the technical field for which organic molecular species can be used for electronic applications (3) (the electroluminescence and the photoluminescence are techniques included in this expression). Further, these compounds can be of use as electron transport materials in OLEDs as well as in other applications. They can be further used as matrix materials for emitters, emitting light from the triplet excited state.

SUMMARY OF THE INVENTION

Object of the present invention are therefore the SBF (spirobifluorene) derivatives, which can be represented by the following formula: SBF-X, wherein:

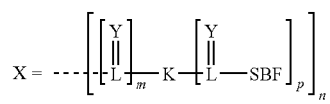

with m=0, 1, 2 or 3;

p=positive integer, preferably 1, 2 or 3, with (p+1) being the valency of K;

n=positive integer, preferably 1, 2, 3 or 4;

L: is the same or different and independently represents C, PR, AsR, SbR, BiR, S, Se, Te, S=Y, Se=Y or Te=Y;

Y: is the same or different and independently represents O, S, Se or Te;

K: is the same or different and independently represents a chemical bond or a group selected from O, S, $BR_{(2-p)}$, N, $NR_{(2-p)}$, $R_{(2-p)}P=O$, $B_3O_3$, $(PR)_3N_3$, $CR_{(3-p)}$, $CR_{(3-p)}(C_6H_4)_{(p+1)}$, $SiR_{(3-p)}(C_6H_4)_{(p+1)}$ with (2-p) and (3-p) being a positive integer including zero; alkane, substituted alkane, alkene, substituted alkene, alkyne, substituted alkyne, aromatic or R substituted aromatic, heteroaromatic or R substituted heteroaromatic or a group originating from benzene and non benzene, monocyclic and polycyclic hydrocarbons which can be bivalent, trivalent or of higher valency; or a combination of two, three or four of the above mentioned groups;

SBF: spiro-compound of formula (I):

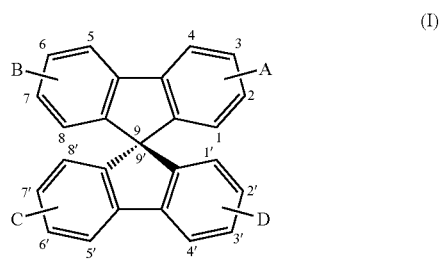

(I)

R, A, B, C, D: is the same or different and independently represents H, deuterium, F, Cl, Br, I, CN, a linear, branched or cyclic alkyl, alkoxy or thioalkoxy chain with 1 to 40 carbon atoms, which can be substituted by $R^1$ and in which one or more non-neighbouring carbon atoms can be replaced by N—$R^1$, O, S, C=O, C=S, C=N$R^1$, Si($R^1$)$_2$, Ge($R^1$)$_2$, O—CO—O, CO—O, CO—N$R^1$, —$CR^1$=$CR^1$— or —C≡C— and in which one or more H-atoms can be replaced by F, Cl, Br, I or CN, or an aromatic or heteroaromatic ring system with 5 to 40 aromatic ring atoms, which can be substituted by deuterium, F, Cl, Br, I, CN or one or more substituents $R^1$, or a combination from two, three or four of these systems; two or more substituents R can form a further monocyclic or polycyclic aliphatic or aromatic ring system with each other;

$R^1$: is the same or different and independently represents H or an aliphatic or aromatic hydrocarbon rest with 1 to 20 C-atoms; wherein the following compounds are excluded:

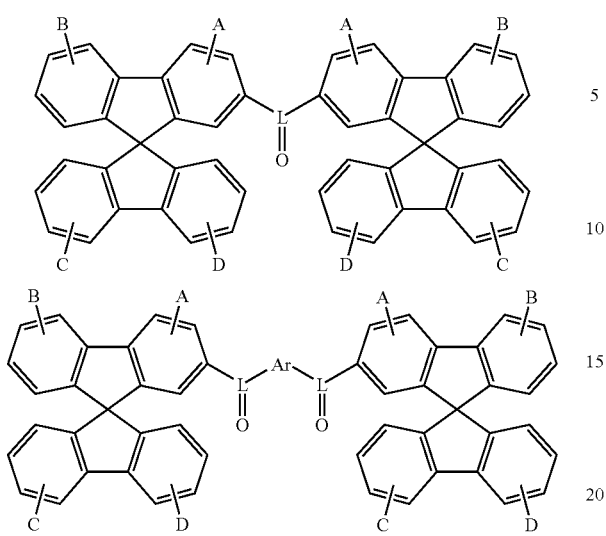

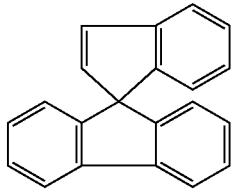

Spiro[9H-fluorene-9,1′-[1H]indene], 309-38-6, SFI (IV)

wherein L, A, B, C and D have the same meaning as above and Ar is the same or different from one another and independently represents a bivalent aromatic or heteroaromatic ring system with 2 to 40 carbon atoms, wherein one or more hydrogen atoms can be replaced by F, Cl, Br or I and which can be substituted by one or more non-aromatic substituents R; two or more substituents R, A, B, C or D on the same ring as well as on different rings, can form a further monocyclic or polycyclic aliphatic or aromatic ring system with each other.

By way of example, the K group coming from benzene and non-benzene, monocyclic and polycyclic hydrocarbons, is preferably selected among: benzene, naphthalene, anthracene, naphthacene, pyrene, perylene, phenanthrene, chrysene, fluoranthene, triphenylene, azulene, 1,1′-biazulene, biphenyl, triphenylamine, triphenylphosphine, triazine, 1,3,5-triphenylbenzene, 1,3,5-triphenyltriazine, furane, thiophene, pyrrole, 1,3,4-oxadiazole, 1,3,4-thiadiazole, diphenyloxadiazole, oxazole, thioazole, aromatic anhydrides, aromatic dianhydrides or adamantane and derivatives. In addition, K can be selected resulting from the following products which each can be substituted by a group R or unsubstituted (each compound being identified in the order from: name, CAS number or bibliographic ref. where known, acronym):

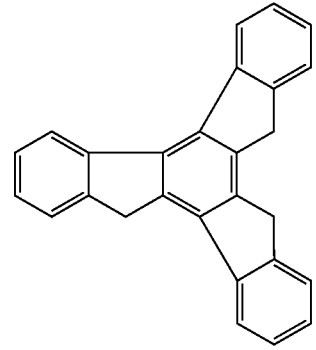

Truxene, 548-35-6, TRX (V)

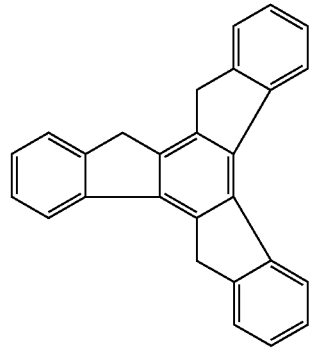

Isotruxene, 17509-71-6, ITRX (VI)

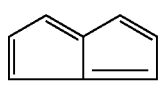

pentalene, 250-25-9, PTN (II)

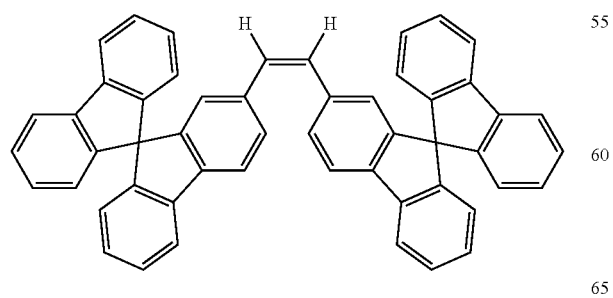

cis-1,2-spirobifluorenylethylene, EP 882082, SBFCST. (III)

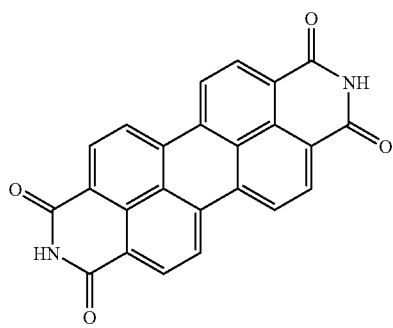

3,4,9,10-Perylenetetracarboxylic 3,4:9,10-diimide, 81-33-4, PTD (VII)

-continued (VIII)

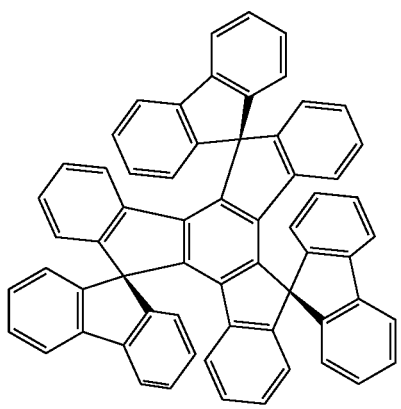

Spirotruxene, SPTRX (IX)

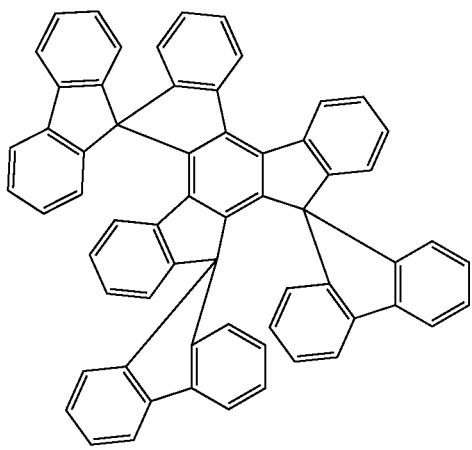

Isospirotruxene, ISPTRX

In a preferred embodiment of the invention, L is the same or different and independently represents C, PR, S or S=Y, particularly preferred C or PR, very particularly preferred C.

In a further preferred embodiment of the invention, Y is the same or different and independently represents O or S, particularly O.

Another object of the invention are the radical anions corresponding to compounds of formula SBF-X. By radical anion is meant the chemical species obtained by addition of one electron to the corresponding neutral species. In the compounds of the present invention, the molecule can gain more than one electron.

Still another object of the invention is a method for preparing the compounds according to the invention and a method for preparing the corresponding radical anions.

Another object of the invention are radical cations corresponding to compounds of formula SBF-X. By radical cation is meant the chemical species obtained by loss of one electron from the corresponding neutral species.

Still another object of the invention are organic electronic devices, OLEDs (organic light emitting diodes), particularly the blue OLEDs and OLEDs emitting light from the triplet state, organic field effect transistors, organic lasers, organic field quenching devices, organic phototransistors, organic photochromic materials, organic solar cells, and components for non linear optics using the compounds according to the invention or the corresponding radical anions.

Further objects of the invention will result apparent from the detailed description of the invention.

DETAILED DESCRIPTION OF THE INVENTION

The present invention relates to compounds of formula SBF-X, as above-specified, to spiro-compounds, wherein at least two SBF groups are connected together through at least a carbonyl group (C=O) and to corresponding derivatives. According to the present invention, by the term derivatives are intended those obtainable according to the classical organic procedure, included therein the corresponding salts, for example as described in (4).

Preferred compounds according to the invention are:
those having more than one L=Y group, wherein said L=Y groups are conjugated with SBF;
those wherein K is alkene or alkyne and n=1;
those wherein K is phenyl or substituted phenyl and p=2;
those wherein K is naphthalene or substituted naphthalene or pyrene or substituted pyrene and p=3;
those wherein K is phenyl, biphenyl, 1-naphthyl, 2-naphthyl, 2-thienyl, 2-furyl, 2-pyrrole.

Within the scope of the present invention and referring to the general formula, particularly preferred are the following compounds:

(X)

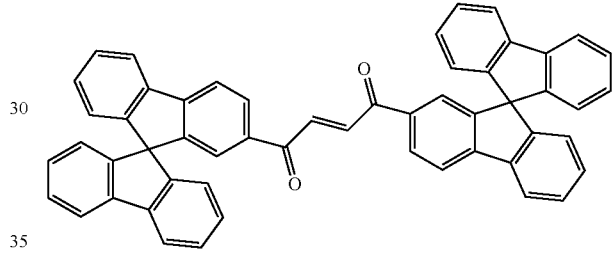

SBF-fumaryl ketone, SBFFK (XIII)

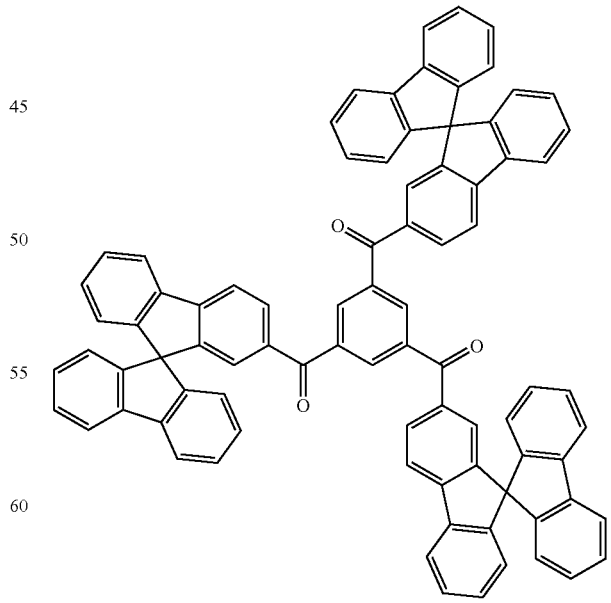

Ph(CO—SBF)$_3$, TRICO

Since some of the molecules of the invention present axial asymmetry, the enantiomers both in a mixture and as pure compounds are included within the scope of the invention.

The compounds of the invention can be prepared starting from commercially available or easily producible compounds according to the classical reactions known to the skilled in the art (4), (8), for example starting from corresponding acyl halides, preferably acid chlorides, through Friedel-Crafts reaction (8). If said acid halides are not commercially available, it is possible to start from the corresponding carboxylic acids in the following manner: to a solution containing a certain quantity of carboxylic acid dissolved in thionyl chloride, a few drops of N,N'-dimethylformamide are added, then the solution is heated under reflux for some hours; after cooling at room temperature, the excess thionyl chloride is removed under reduced pressure, then petroleum ether is added and a vacuum distillation is executed to obtain the corresponding acid chloride.

The following SBF bonding occurs with the conventional methods, as above-mentioned.

As above-mentioned, a method for preparing the compounds of the invention involves the Friedel-Crafts acylation (8) of SBF, using aluminum chloride $AlCl_3$ as a catalyst or another analogous catalyst and includes the following stages:

select the acyl halide depending on the final compound to be obtained and place it in a solvent, preferably dichloromethane, at a temperature not above 15-20° C., preferably in a water/ice bath;

add SBF, if necessary functionalized, preferably dropwise and under stirring, and heat under reflux to complete the reaction;

take up the final compound by adding to the reaction mixture a diluted aqueous solution of a mineral acid, preferably HCl;

separate the organic phase and repeat the extraction operation, collecting all the organic extracts in which the final product is contained, obtainable through conventional techniques, such as crystallization or solvent evaporation.

The optimal conditions for obtaining the desired compounds are within the reach of the skilled in the art.

In case of intermediates (II) to (IX), it is possible to start from the SBF acid chloride.

The anionic radicals of the compounds of the invention are preferably obtained by chemical or electrochemical way with the addition of an electron to the corresponding neutral compound; the electrochemical way is particularly preferred because of its selectivity and easiness of execution.

For obtaining dianionic diradicals, when it is possible, which can be paramagnetic species, it is enough to operate at more negative potentials with respect to those relating to the radical anions, shown by the experimental conditions.

An example of radical anions is given in the experimental part in example 6.

The electrochemical method for obtaining the radical anions is generally described in (5) and (6). Such method is carried out by using an electrochemical cell having two compartments: an anodic one and a cathodic one; in the cathodic one a working electrode and a reference calomel electrode are placed. An aprotic solvent or mixtures of typically N,N-dimethylformamide, acetonitrile, tetrahydrofuran, N-methylpyrrolidone, dimethylsulfoxide, preferably N,N-dimethylformamide, acetonitrile and, particularly preferably N,N-dimethylformamide, is made anhydrous according to the usual procedures (5), to this a support electrolyte is added, typically tetraethylammonium perchlorate, tetrabutylammonium tetrafluoroborate, lithium perchlorate, particularly preferably tetraethylammonium perchlorate, which is made anhydrous as well, so as to obtain a concentration between 1 M and 0.01 M, preferably 0.2M and 0.05M, with particular preference about 0.1M.

The electrolytic solution thus prepared is placed in the cathodic compartment which is separated from the anodic one through a portion of the same electrolytic solution, properly gelled, and in which the anode is present (Pt net).

The selected compound is added to the electrolyte solution present in the cathodic compartment of a divided cell, under a nitrogen flow, in such a way to obtain a concentration between 0.01 M and 0.1 mM, preferably between 0.01 M and 0.5 mM and with particular preference 1 mM. In the cathodic compartment of the cell a reticulated vitreous carbon (RVC) electrode, as a cathode, and a calomel electrode (SCE) as a reference electrode are placed. In the anodic compartment of the cell, which is divided from the cathodic compartment by means of a gelled electrolyte solution, a preferably platinum-net electrode is placed as an anode. Other electrode materials usable as working electrode are: mercury, lead, silver, Ti-based composite materials, conductive carbon materials, carbon-containing conductive materials, chemically modified electrodes, particularly preferred is the glassy carbon for the following features: wide applicable d.d.p. window, inexpensiveness, non toxicity and easiness of use.

The usable carrier electrolytes are those preferably containing: perchlorate anions, tetrafluoroborate anions, hexafluorophosphate anions, lithium cations, sodium cations, tetraalkylammonium cations and respective mixtures; particularly preferred are perchlorate anions and tetraethylammonium cations.

Between the electrodes a proper d.d.p. is applied, so as to obtain the desired radical anion, generally a d.d.p. of about 0.2 V more negative than the standard potential E° of the compound to be treated (vs SCE).

The working temperatures can be between −20° C. and +50° C.; particularly preferred is room temperature.

The compounds of the invention, due to the presence of the C=O group/s interposed between the SBF groups, form more easily the radical anions with respect to the corresponding compounds wherein C=O is not present.

In fact, it has been observed that the introduction of the functional conjugated C=O group has, as a consequence, a remarkable improvement of the molecule property, because it confers thereto an increase in the "electron acceptor" feature, by shifting the standard potential, E°, of the molecule towards more positive (lower) values. It is known that the standard potential, E°, defined as in (6), shifts towards more positive values with respect to a reference molecule when its properties as electron-acceptor are improved based on the reference molecule.

Referring to the compounds, corresponding derivatives and salts according to the present invention and to corresponding radical anions, the standard potential E° shifts towards more positive values of the ΔE° quantity. The ΔE° increment towards more positive potentials with respect to values of corresponding compounds without the functional C=O group has the advantage that the uses of the molecule of the invention involve an energy saving. The compounds of the invention and the corresponding radical anions, due to the presence of a plurality of conjugated C=O groups, can be generally advantageously employed in the electroluminescence field, particularly for light-emitting diodes (OLEDs), more particularly blue-light OLEDs and OLEDs emitting from the triplet state, as electron transporting materials in OLEDs as well as in other applications, as molecular switching components, for non linear optics, in molecular-based computational systems (this latter described in Aviram, ref. (1)), in field-effect transistors (FET) (7), in negative differential resistance (NDR) semiconductors. Just for the presence of many conjugated C=O groups, the compounds of the invention allow the easy transfer of more electrons with respect to similar compounds, thus allowing to obtain anionic species usable as molecular magnets.

The compounds of the invention, preferably in the enantiomeric form, can be used for applications in molecular biology and in nanotechnologies related to this latter. The compounds according to the invention can be applied in form of thin film or coating upon a proper substrate (metallic or non metallic) according to techniques (for example chemical, physical-chemical, physical) known to those skilled in the art. The devices carry at least an active layer including at least one compound of the invention, applied on said substrate.

The organic electronic device is preferably selected from the group consisting of organic and polymeric light emitting diodes (OLEDs, PLEDs), organic field-effect transistors (O-FETs), organic thin film transistors (O-TFTs), organic light emitting transistors (O-LETs), organic integrated circuits (O-ICs), organic solar cells (O-SCs), organic field quench devices (O-FQDs) or organic laser diodes (O-Laser). Particularly preferred are organic or polymeric light emitting diodes.

The compounds can be applied on the substrate of the organic electronic device by sublimation, preferably at a pressure below $10^{-5}$ mbar, more preferably below $10^{-6}$ mbar, most preferably below $10^{-7}$ mbar.

The compounds can further be applied on the substrate of the organic electronic device by the OVPD (organic vapour phase deposition) process or by means of a train sublimation. The materials are applied with these methods at a pressure between $10^{-5}$ mbar and 1 bar.

The compounds can further be applied on the substrate of the organic electronic device from solution, e.g. by spin-coating, or by a printing method, such as offset-printing, or preferably by LITI (light induced thermal imaging) order by ink-jet printing.

The following examples are given by way of illustration of the invention and are not to be considered limiting of the same.

EXAMPLES

Reagents and instruments: carbon sulfide ($CS_2$) Carlo Erba; aluminum trichloride ($AlCl_3$) Fluka; thionyl chloride ($SOCl_2$) Merck; IR: Perkin-Elmer 298, Shimadzu 470; NMR; Bruker AC 200. All the acid chlorides used are Aldrich, 2-bromobiphenyl and truxenone are Lancaster products.

Example 1

Preparation of SBF (COC=CCO) SBF (SBF-fumaryl ketone) (X)

To 110 mg fumaryl chloride (d=1.413 g/ml; 0.08 ml) in 20 ml $CH_2Cl_2$, 210 mg of finely pulverized anhydrous $AlCl_3$ is added at 15° C. (water-ice bath) (black colour). A solution containing 500 mg 9,9'-spirobifluorene in 20 ml $CH_2Cl_2$ is added dropwise under stirring within 30 minutes and is allowed to reach RT (room temperature) (red-blue colour). Then, the mixture is heated under reflux and the stirring is maintained for two more hours. After treatment with water and ice and then with diluted HCl, the organic phase is separated (orange colour). The organic extracts are treated with saturated sodium carbonate, washed with water and dried on anhydrous sodium sulphate. Column chromatography, eluent 25% ethyl acetate/hexane (plate at 30% with the same eluents).

$^{13}$C-NMR (CDCl$_3$, 50 MHz, δ [ppm] vs SiMe$_4$): 191.6 (CO), 150.2, 149.3, 147.6, 146.9, 141.8, 140.3, 135.7, (all quaternary carbon atoms); 135.2, 129.2, 127.9, 124.2, 123.9, 120.9, 120.0, 119.8 (all CH); 65.6 (C-spiro).

Example 2

Preparation of Ph(1.3-CO-SBF)$_2$ (1,3-DICO) (XI)

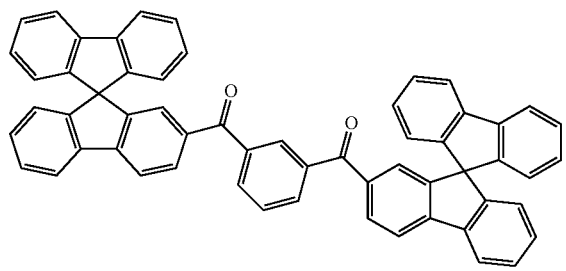 [SMILES: O=C(c1cccc(C(=O)c2ccc3c(c2)C2(c4ccccc4-c4ccccc42)c2ccccc2-3)c1)c1ccc2c(c1)C1(c3ccccc3-c3ccccc31)c1ccccc1-2]

To 353 mg isophthaloyl chloride (1.74 mmols) in 20 ml $CH_2Cl_2$, 232 mg of finely pulverized anhydrous $AlCl_3$ (1.74 mmols) is added at 15° C. (water-ice bath) (yellow colour). A solution containing 250 mg 9,9'-spirobifluorene (0.79 mmols) in 10 ml $CH_2Cl_2$ is added dropwise and under stirring within 30 minutes and is allowed to reach RT (red colour). Then, the mixture is heated under reflux and the stirring is maintained for two more hours. After treatment with water and ice and then with diluted HCl the organic phase is separated (white colour). The organic extracts are treated with saturated sodium carbonate, washed with water and dried on anhydrous sodium sulphate. Column chromatography, eluent 40% $CH_2Cl_2$/hexane (plate at 60% with the same eluents).

$^1$H-NMR (CDCl$_3$, 200 MHz, δ [ppm] vs SiMe$_4$): 7.62-8.22 (34 H, mc, ArH)

$^{13}$C-NMR (CDCl$_3$, 50 MHz, δ [ppm] vs SiMe$_4$): 193.6 (CO), 65.8 (spiro C).

Example 3

Preparation of Ph(1.4-CO-SBF)$_2$ (1,4-DICO) (XII)

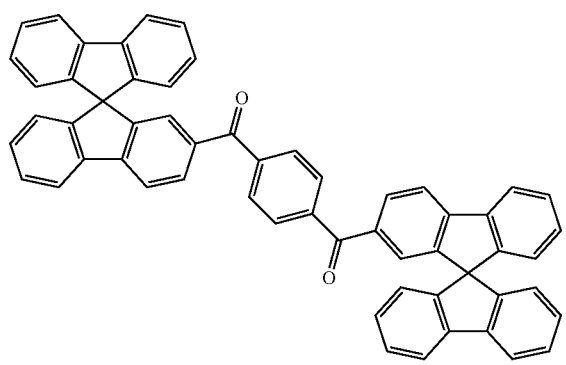 [SMILES: O=C(c1ccc(C(=O)c2ccc3c(c2)C2(c4ccccc4-c4ccccc42)c2ccccc2-3)cc1)c1ccc2c(c1)C1(c3ccccc3-c3ccccc31)c1ccccc1-2]

To 353 mg terephthaloyl chloride (1.74 mmols) in 20 ml $CH_2Cl_2$, 232 mg of finely pulverized anhydrous $AlCl_3$ (1.74 mmols) are added at 15° C. (water-ice bath) (yellow colour).

A solution containing 250 mg 9,9'-spirobifluorene (0.79 mmols) is added dropwise in 10 ml $CH_2Cl_2$ and under stirring within 30 minutes and is allowed to reach RT (red colour). Then, the mixture is heated under reflux and the stirring is maintained for two more hours. After treatment with water and ice and then with diluted HCl the organic phase is separated (white colour). The organic extracts are treated with saturated sodium carbonate, washed with water and dried on anhydrous sodium sulphate. Column chromatography, eluent 40% $CH_2Cl_2$-hexane (plate at 60% with the same eluents).

$^1$H-NMR ($CDCl_3$, 200 MHz, δ [ppm] vs $SiMe_4$): 6.82-8.22 (34 H, mc, ArH)

$^{13}$C-NMR ($CDCl_3$, 50 MHz, δ [ppm] vs $SiMe_4$): 195.2 (CO), 65.8 (spiro C).

Example 4

Preparation of Ph(CO-SBF)$_3$ (TRICO) (XIII)

To 1.26 g 1,3,5-benzenetricarbonyl trichloride (4.74 mmols) in 20 ml $CH_2Cl_2$, 843 mg of finely pulverized anhydrous $AlCl_3$ (6.32 mmols) is added at 15° C. (water-ice bath) (yellow colour). A solution containing 500 mg 9,9'-spirobifluorene (1.58 mmols) in 10 ml $CH_2Cl_2$ is added dropwise and under stirring within 30 minutes and is allowed to reach RT (green-orange-red colour). Then, the mixture is heated under reflux and the stirring is maintained for two more hours. After treatment with water and ice and then with diluted HCl the organic phase is separated. The organic extracts are treated with saturated sodium carbonate, washed with water and dried on anhydrous sodium sulphate; a yellow waxy liquid is obtained. Column chromatography, eluent 40% $CH_2Cl_2$-hexane (plate at 60% with the same eluents).

$^{13}$C-NMR ($CDCl_3$, 50 MHz, δ [ppm] vs $SiMe_4$): 191.5 (CO), 65.6 (spiro C).

Example 5

Preparation of Tri-Spirobifluorene (Spirotruxene) (VIII)

To a solution of 2-bromobiphenyl (14.3 mmols; 0.9 g; 2.4 ml) dissolved in 20 ml anhydrous THF is added at −78° C. n-BuLi (32.5 mmol; 2.5 M in hexane; 13 ml) within 30 minutes, then it is brought to 0° C. By means of a syringe, the lithiated compound is transferred in a dropping funnel of a second flask wherein a Truxenone suspension is contained (1.3 mmol; 0.5 g) dissolved in 30 ml anhydrous THF, and is slowly added at 0° C. The solution is brought at room temperature, maintained at this temperature for 4 h and then treated with a saturated solution of $NH_4Cl$. The aqueous solution is extracted with $CH_2Cl_2$ (3×15 ml), the organic phases are dried over anhydrous sodium sulphate. After vacuum evaporation of the solvent a reddish liquid is obtained, isomers mixture. The liquid is dissolved in 10 ml of glacial acetic acid and the mixture is heated under reflux, then a few drops of conc. HCl are added and it is refluxed for one more minute. Then, water is added until turbidity, it is allowed to cool, filtered over Gooch. The acid aqueous phase is extracted with $CH_2Cl_2$ and dried over anhydrous sodium sulphate, then it is dried in the rotavapor. A beige precipitate is obtained insoluble in the common solvents (850 mg). From the NMR spectrum of the precipitate in DMSO it results to be the Spirotruxene (yield of 78%).

Spirotruxene (VII):

$^1$H-NMR (DMSO, 200 MHz): 7.62-7.27 (36 H, m, ArH).

$^{13}$C-NMR (DMSO, 50 MHz): 141.35, 141.21, 140.17, 139.46 (all quaternary carbon atoms); 129.56, 129.09, 128.79, 127.99, 127.28, 126.70, 126.60, 125.55 (all CH).

Example 6

Radical anions and the corresponding E° are shown in the following Table 1:

TABLE 1

| Products | E° (V vs SCE) |
| --- | --- |
| Cis-1,2-di-spirobifluorenyl-ethylene (III) | −1.95 |
| SPIROTRUXENE (VIII) | −2.55 |
| SBF FUMARYL KETONE (X) | −1.18 |
| 1,3-DICO (XI) | −1.50 |
| 1,4-DICO (XII) | −1.40 |
| TRICO (XIII) | −1.48 |

REFERENCES

1. Haas G. and Prelog V., Helv. Chim. Acta (1969) 52, 1202-1218.
2. Aviram A et al., J. Am. Chem. Soc. (1988) 110, 5687-92.
3. "Molecular Electronics: science and technology" A. Aviram and M. Ratner editors, Annals of the New York Academy of Science Vol. 1852 (1998)
4. B. S. Furniss, A. J. Annaford, P. W. G. Smith and A. R. Tatchell in: Vogel's textbook of practical organic chemistry, 5th ed, Longman, UK 1989.
5. Organic Electrochemistry", $4^a$ Ed., Henning Lund e Ole Hamerich Eds., Marcel Dekker Inc, NY, (2001).
6. A. J. Bard, L. R. Faulkner, "Electrochemical methods" Wiley, New York. II ed. 2001.
7. J. G. Laquindanum, H. E. Katz, A. Dodabalapur and A. J. Lovinger, J. Am. Chem. Soc., (1996) 118, pp 11331-11332.
8. Gore P. H., Chem. Rev. (1955), 55, p. 229.

The invention claimed is:

1. Spirobifluorene (SBF) derivatives having the following formula: SBF-X wherein:

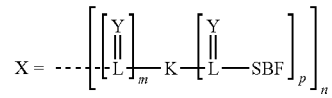

with m=0, 1, 2 or 3;

p=positive integer, with (p+1) being the valency of K;

n=1;

L: is the same or different and independently represents C or PR;

Y: is the same or different and independently represents O, S, Se or Te;

K: is the same or different and independently represents a chemical bond or a group selected from alkane, alkene, alkyne, aromatic or R substituted aromatic, heteroaromatic or R substituted heteroaromatic or a monocyclic or polycyclic hydrocarbon group;

SBF: spiro-compound of formula (I):

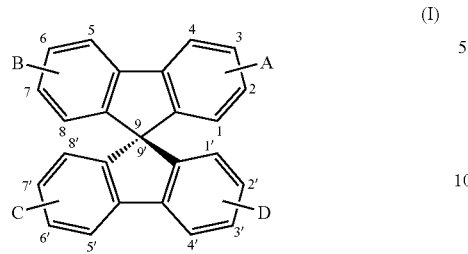

A, B, C and D: are the same or different and independently represents H, deuterium, F, Cl, Br, I, CN, a linear, branched or cyclic alkyl, alkoxy or thioalkoxy chain with 1 to 40 carbon atoms, which is optionally substituted by $R^1$ and in which one or more non-neighboring carbon atoms can be replaced by N—$R^1$, O, S, C=O, C=S, C=N$R^1$, Si($R^1$)$_2$, Ge($R^1$)$_2$, O—CO—O, CO—O, CO—N$R^1$, —C$R^1$=C$R^1$— or —C≡C— and in which one or more H-atoms is optionally replaced by F, Cl, Br, I or CN, or an aromatic or heteroaromatic ring system with 5 to 40 aromatic ring atoms, which is optionally substituted by deuterium, F, Cl, Br, I, CN or one or more substituents $R^1$, or a combination from two, three or four of these systems; two or more substituents R optionally forms a further monocyclic or polycyclic aliphatic or aromatic ring system with each other;

R is the same or different and independently represents H, deuterium, F, Cl, Br, I, CN, a linear, branched or cyclic alkyl chain with 1 to 40 carbon atoms, or an aromatic or heteroaromatic ring system with 5 to 40 aromatic ring atoms, which is optionally substituted by deuterium, F, Cl, Br, I, CN or one or more substituents $R^1$;

$R^1$: is the same or different and independently represents H or an aliphatic or aromatic hydrocarbon ring with 1 to 20 C-atoms; wherein the following compounds are excluded:

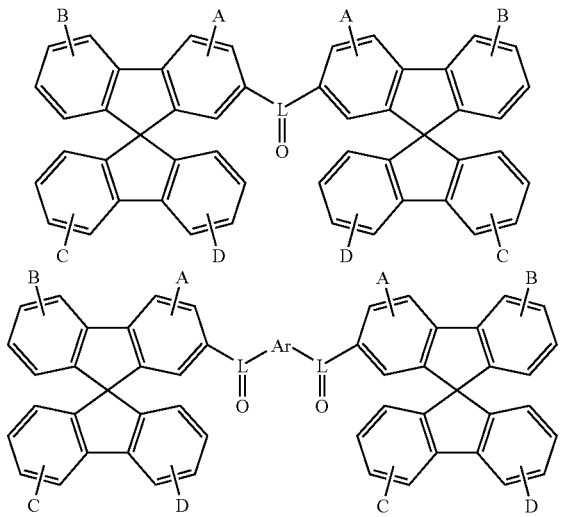

wherein L, A, B, C and D have the same meaning as above and Ar is the same or different from one another and independently represents a bivalent aromatic or heteroaromatic ring system with 2 to 40 carbon atoms, wherein one or more hydrogen atoms is optionally replaced by F, Cl, Br or I and which is optionally substituted by one or more non-aromatic substituents R; two or more substituents R, A, B, C or D on the same ring as well as on different rings, optionally forms a further monocyclic or polycyclic aliphatic or aromatic ring system with each other.

2. The SBF derivatives according to claim 1, wherein K is benzene, naphthalene, anthracene, naphthacene, pyrene, perylene, phenanthrene, chrysene, fluoranthene, triphenylene, azulene, 1,1'-biazulene, biphenyl, triphenylamine, triphenylphosphine, triazine, 1,3,5-triphenylbenzene, 1,3,5-triphenyltriazine, furane, thiophene, pyrrole, 1,3,4-oxadiazole, 1,3,4-thiadiazole, diphenyloxadiazole, oxazole, thioazole, aromatic anhydrides, aromatic dianhydrides or adamantane.

3. The SBF derivatives according to claim 1, wherein L is the same or different and independently represents C.

4. The SBF derivatives according to claim 1, wherein Y is the same or different and independently represents O or S.

5. The SBF derivatives according to claim 1, selected from the compounds having the following formulas:

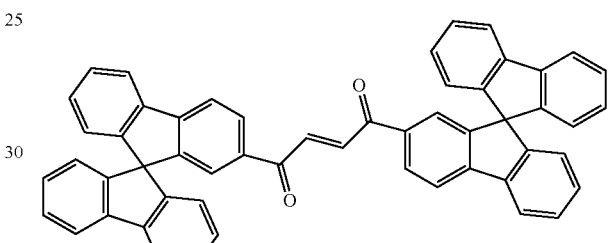

(X)
SBF-fumaryl ketone, SBFFK

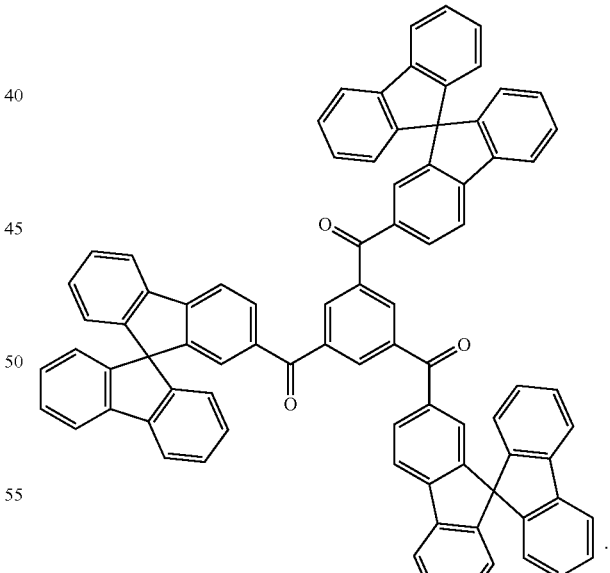

(XIII)
Ph(CO—SBF)$_3$, TRICO

6. The SBF derivatives according to claim 1, wherein p=1, 2 or 3.

7. Enantiomers both in a mixture between them and as pure compounds which comprises the SBF derivatives according to claim 1.

8. An electronic device which comprises SBF derivatives according to claim 1.

9. The device as claimed in claim 8, wherein the device is molecular-based computational systems, OLEDs, components for non linear optics including compounds, in field-effect transistors, in negative differential resistance semiconductors, or molecular magnets 10. The device as claimed in claim 8, wherein said OLEDs are blue OLEDs or OLEDs emitting light from the triplet state.

11. The SBF derivatives according to claim 1, wherein Y=O.

12. The SBF derivatives according to claim 1, selected from the compounds:
- having more than one L=Y group, wherein said L=Y groups are conjugated with SBF;
- those wherein K is alkene or alkyne;
- those wherein K is phenyl or substituted phenyl and p=2;
- those wherein K is naphthalene or substituted naphthalene and p=3;
- those wherein K is phenyl, biphenyl, 1-naphthyl, 2-naphthyl, 2-thienyl, 2-furyl, or 2-pyrrole.

13. A method for the preparation of SBF derivatives according to claim 1, which comprises the following stages:
- selecting the acyl halide depending on the final compound to be obtained and placing it in a solvent, at a temperature not above 15-20° C.;
- adding SBF, and optionally functionalized and under stirring, and reflux to complete the reaction;
- extracting the final compound by adding to the reaction mixture a diluted aqueous solution of a mineral acid;
- separating the organic phase and repeat the extraction operation, collecting all the organic extracts in which the final product is contained, obtainable through conventional techniques.

14. The method as claimed in claim 13, wherein which comprises the following stages:
- selecting the acyl halide depending on the final compound to be obtained and placing it in dichloromethane, at a temperature not above 15-20° C., in a water/ice bath;
- adding SBF, and optionally functionalized, dropwise and under stirring, and reflux to complete the reaction;
- extracting the final compound by adding to the reaction mixture a diluted aqueous solution of a HCl;
- separating the organic phase and repeat the extraction operation, collecting all the organic extracts in which the final product is contained, obtainable through conventional techniques.

15. The method according to claim 13, wherein the acyl halide is obtained starting from the corresponding carboxylic acid.

16. The method according to claim 13, wherein the conventional techniques are crystallization or solvent evaporation.

17. The method according to claim 14, wherein the conventional techniques are crystallization or solvent evaporation.

* * * * *